United States Patent

Kurtz et al.

[11] Patent Number: 5,236,425
[45] Date of Patent: Aug. 17, 1993

[54] SELF-ADJUSTING SUCTION REGULATOR

[75] Inventors: Robert J. Kurtz, New York; Joseph LiCausi, Port Jefferson Station, both of N.Y.

[73] Assignee: BioResearch, Inc., Farmingdale, N.Y.

[21] Appl. No.: 574,113

[22] Filed: Aug. 29, 1990

[51] Int. Cl.[5] .................................................. A61M 1/00
[52] U.S. Cl. ................................... 604/320; 604/317; 137/513.7
[58] Field of Search ............... 137/513.3, 513.7, 519.5, 137/526, 543.17; 604/317-322

[56] References Cited

U.S. PATENT DOCUMENTS

| | | | |
|---|---|---|---|
| 564,165 | 7/1896 | Stage | 137/533.27 |
| 1,144,657 | 6/1915 | Keller | 137/513.7 |
| 3,363,626 | 1/1968 | Bidwell. | |
| 3,937,250 | 2/1976 | Golan et al. | 137/543.17 |
| 4,310,016 | 1/1982 | Aubel | 137/513.7 |
| 4,605,400 | 8/1986 | Kurtz et al.. | |
| 4,675,011 | 6/1987 | Kurtz et al.. | |

Primary Examiner—Randall L. Green
Assistant Examiner—R. Clarke
Attorney, Agent, or Firm—Larson & Taylor

[57] ABSTRACT

A suction regulator is provided for a pleural drainage device which includes a spring-loaded valve which opens to atmosphere to maintain the appropriate suction levels in the pleural drainage device together with an air flow regulator which reduces the air flow to the drainage device when the suction level from the suction source exceeds a predetermined level. A tapered passageway is provided in the air flow path from the suction source to the pleural drainage device and a ball valve having an opening therethrough is slidably disposed within the tapered passageway so that when the air flow through the passageway increases, the ball valve rises to decrease the amount of air passing through the passageway.

8 Claims, 2 Drawing Sheets

SELF-ADJUSTING SUCTION REGULATOR

FIELD OF THE INVENTION

The present invention relates generally to surgical drainage devices provided with suction control mechanisms to maintain the suction levels within the drainage device at appropriate levels.

BACKGROUND OF THE INVENTION

Pleural drainage devices which are used to maintain the appropriate suction level within the pleural cavity of a patient are well-known. The first unitary device developed for collecting fluids from the pleural cavity and controlling the suction level within the pleural cavity is disclosed in U.S. Pat. No. 3,363,626. This apparatus provides three chambers, one chamber comprising a collection chamber for collecting the fluids drained from the pleural cavity through a thoracotomy tube, a second chamber known as an underwater seal chamber which protects the pleural cavity from being subject to atmospheric pressure, and a third chamber known as a pressure manometer chamber which serves to regulate the degree of negative pressure within the pleural cavity. This type of apparatus has been highly successful in both removing fluids from the pleural cavity and in maintaining the desired degree of negativity within the pleural cavity.

However, the apparatus disclosed in U.S. Pat. No. 3,363,626 required prefilling of an underwater seal chamber with water as well as prefilling of the manometer chamber to the desired level to maintain the desired degree of negativity within the pleural cavity. U.S. Pat. No. 4,605,400 discloses a pleural drainage apparatus which eliminates the underwater seal chamber and the water filled manometer chamber to regulate the degree of suction. This patent discloses the use of one-way valves which perform the function of preventing atmospheric air from entering the collection chamber and separate one-way valves which open to admit atmospheric air to the passageway between the collection chamber and the suction source to maintain the desired degree of negativity within the collection chamber.

In practice, it has been found that the suction level from the suction source in a hospital varies over a wide range dependent upon the degree of use of the suction available. Under these circumstances, it is difficult to maintain the desired degree of negativity within the collection chamber and the patient's pleural cavity with any precise degree of accuracy. While the valve means disposed within the pleural cavity shown in U.S. Pat. No. 4,605,400 can maintain the degree of negativity at an appropriate level when the suction source is providing suction within a normal range, when a very high degree of suction is provided by the suction source, the valves cannot provide sufficient air flow to maintain the desired degree of negativity.

SUMMARY OF THE INVENTION

According to the present invention there is provided an air flow regulator which restricts the air flow to the pleural drainage device when the suction source produces a very high level of suction. The air flow regulator, by restricting the passageway from the suction source, permits the suction regulating means within the pleural drainage device to maintain the desired degree of negativity within the collection chamber and the patient's pleural cavity. Thus, the combination of the two separate suction regulating devices, the problems associated with prior art devices are overcome.

More specifically, according to one embodiment of the present invention an air flow regulator is provided including a tube having a tapered passageway therein, the tube having a valve seat at each end thereof with a ball valve disposed within the tube. As the suction from the suction source increases to provide greater air flow through the passageway, the ball valve will rise and as it rises the air flow path through the tube decreases due to the tapered passageway. Thus, the air flow through the passageway is decreased, permitting the suction regulator within the pleural drainage device to maintain a desired degree of negativity within the pleural drainage device.

In another embodiment of the invention the ball valve is provided with an aperture therethrough and a guide rod extends through the tube. The ball valve is slidable on the rod and travels the length of the tube. The aperture through the ball valve has a considerably larger diameter than the guide rod extending through the aperture so that even when the ball is seated at either end of the tube, air will pass through the aperture.

The suction regulator unit within the pleural drainage device also comprises a chamber with tapered walls and a tapered valve which is spring pressed into an opening in the bottom wall of the chamber which communicates with atmosphere. When the degree of negativity within the drainage device reaches an excessive level, the valve within the suction regulator unit rises to admit atmospheric air. The combination of the suction regulator unit together with the air flow regulator permits the desired degree of negativity to be maintained within the collection chamber and the patient's pleural cavity irrespective of the level of suction being delivered by the suction source.

An object of the present invention is to provide a device which will maintain the proper suction level within a pleural drainage device and a patient's pleural cavity irrespective of wide fluctuations in the level of suction delivered by the suction source.

Another object of the present invention is to provide suction regulating means for a pleural drainage device which includes a suction regulator which opens to admit atmospheric air to decrease the level of suction in combination with an air flow regulator which reduces the air flow from the suction source to prevent a high degree of suction being delivered to the pleural drainage device.

Other objects and many of the attendant advantages will become apparent upon consideration of the following detailed specification in connection with the accompanying drawings wherein:

DETAILED DESCRIPTION OF THE PREFERRED EMBODIMENT

Figure 1:
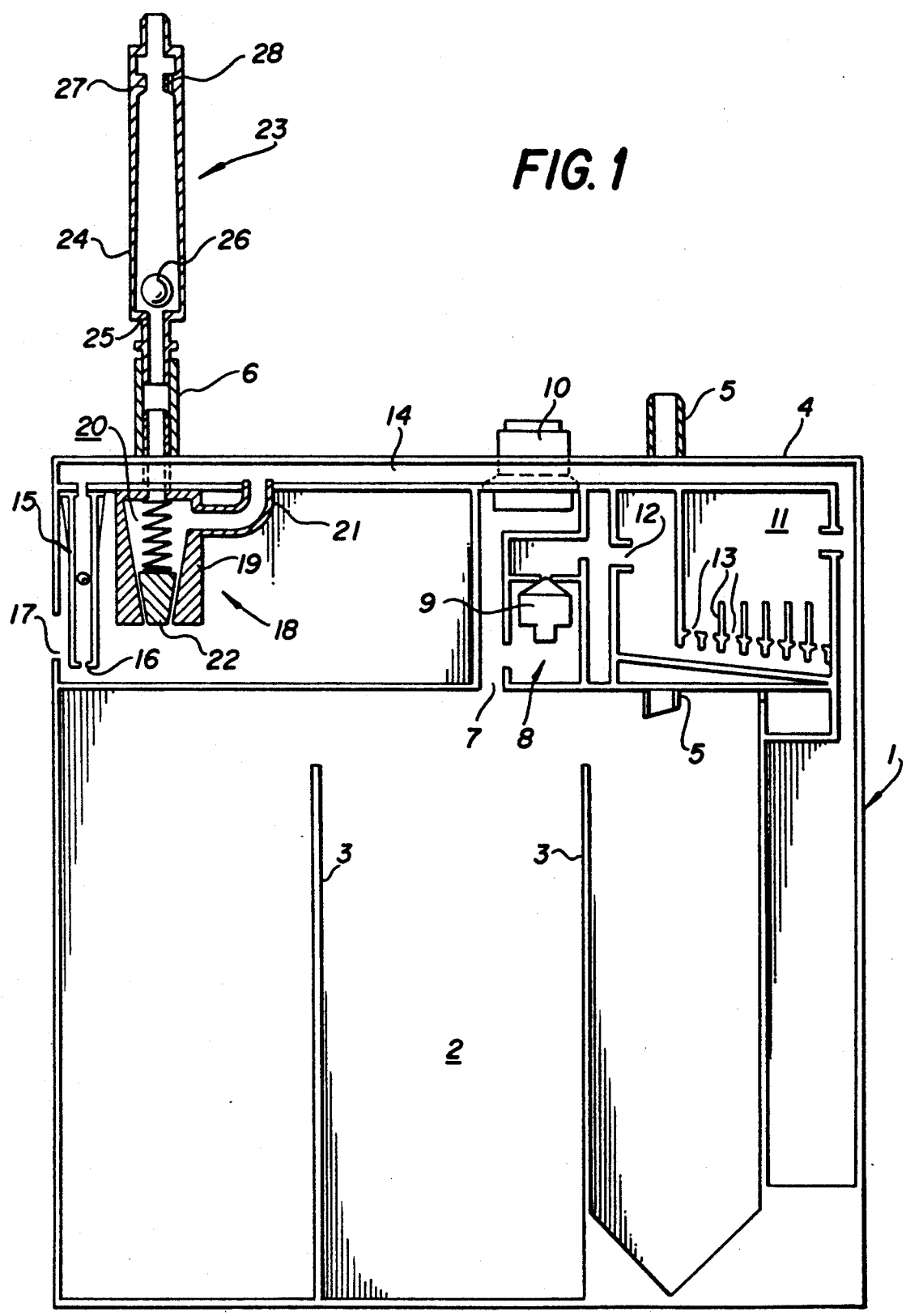
FIG. 1 is a front elevation view in cross section of a drainage device according to the present invention and FIG. 2 is a cross sectional view of another embodiment of the air flow regulator shown in FIG. 1.

Referring now more specifically to the drawings where like numerals indicate like parts throughout the several views there is shown at 1 in FIG. 1 a pleural drainage device which is generally similar to the apparatus disclosed in U.S. Pat. No. 4,605,400.

The lower portion of the drainage device comprises a collection chamber 2 which is divided into three separate compartments by means of partitions 3. The top wall 4 of the drainage device has an inlet tube 5 therein which is in communication with the collection chamber 5 as shown in FIG. 1. A rubber tube may connect the inlet 5 with the thoracic cavity of a patient so that fluids collecting within the pleural cavity may pass through the tube and inlet 5 into the collection chamber 2.

In order to keep the lungs of the patient expanded, it is necessary to maintain a certain degree of negativity within the pleural cavity. It can be seen that there is provided an outlet tube 6 in the top wall 4 of the drainage device, the outlet tube being connected with a suction source. The outlet tube 6 is in communication with the collection chamber 2 and with the patient's pleural cavity through inlet 5 and the thoracotomy tube connected with the inlet tube 5. The collection chamber 2 has an outlet 7 at the upper end thereof and air passes from the collection chamber through the outlet 7 and into a trap chamber 8 which prevents any fluids within the collection chamber from entering one-way valve means 9 at the upper end of trap chamber 8. The specific structure of the one-way valve 9 is shown and described in U.S. Pat. No. 4,605,400 and this valve means 9 provides the function of permitting gases to pass through the one-way valve towards the suction source but prevents reverse passage of gases through the valve.

There is also shown in FIG. 1 an excess negativity valve 10 which is in communication with the outlet 7 from the collection chamber 2. In the event there is an excessive degree of negativity within the patient's pleural cavity, the valve 10 may be open to permit a metered amount of atmospheric air to enter the collection chamber. The specific structure of this valve is shown in FIG. 6 of U.S. Pat. No. 4,605,400.

Gases passing through the one-way valve 9 enter an air leak indicator 11 through passageway 12. The air leak indicator 11 is provided with a series of passageways 13 and liquid is provided in the air leak chamber so that the degree of air leak within the patient's pleural cavity may be determined by the number of passageways 13 through which gases are bubbling. The detailed structure and operation of the air leak indicator is more fully described in U.S. Pat. No. 3,683,913.

Figure 2:
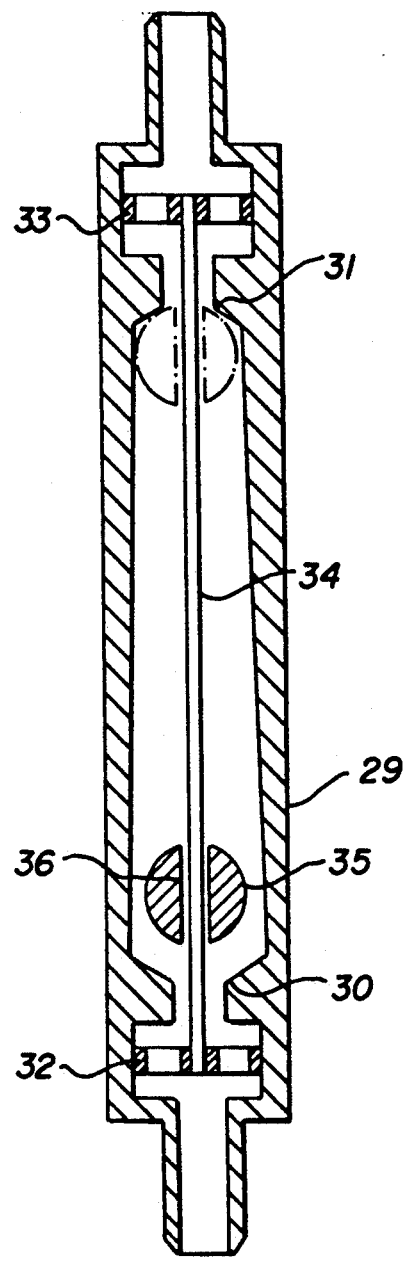

There is shown at 14 a passageway which extends from the outlet of the air leak indicator 11 to the opposite end of the drainage device. There is provided a tube 15 at the end of the passageway 14 which serves as a suction indicator. The lower end of the tube 15 has a small opening 16 which communicates with outside atmospheric air through an opening 17. The upper end of the tube 15 communicates with passageway 14 so that atmospheric air passes up through tube 15 and into passageway 14. A ball is disposed within tube 15 and the position of the ball within tube 15 is indicative of the degree of negativity being maintained within the drainage device. This device is shown in FIG. 2 of U.S. Pat. No. 4,605,400 and is fully described in the specification of this patent.

The suction regulator unit 18 comprises a housing member 19 having an internal chamber 20 which has tapered side walls. The chamber 20 communicates at the upper end with the outlet tube 6 and communicates with the passageway 14 through a connecting tube 21. A valve member 22 is provided with a tapered outer surface which conforms with the taper of the surface of chamber 20 and the valve member 22 is spring pressed to retain the valve so as to close the opening in the lower end of the housing member 19. In operation, when the atmospheric pressure applied to the bottom surface of the valve member 22 is greater than the pressure on the upper surface of the valve due to the spring and a reduced pressure within the collection chamber, the valve opens to admit atmospheric air up through the outlet tube 6 to suction so as to reduce the degree of negative pressure within the drainage device.

In addition to the suction regulator unit 18, there is provided an air flow regulator 23 which is disposed in the suction line leading to the suction source. The air flow regulator 23 comprises a tubular housing member 24 having a tapered internal surface so that the internal diameter of the tubular member is substantially greater at the lower end of the tube than at the upper end. The lower end of the tube 24 has a reduced passageway which forms a valve seat 25 for ball valve 26. At the upper end of the tubular housing member 24, there is provided a valve seat 27 which has a restricted passageway 28 on one side thereof.

In operation, when the pleural drainage apparatus with the air flow regulator 23 is connected to a suction source, the suction will cause the ball valve 26 to rise off the valve seat 25 so as to permit gases to pass from the drainage device through the tubular housing member 24 to the suction source. As the level of suction from the suction source rises, the ball 26 will move upwardly through the housing member 24. This upward movement will, due to the tapered walls of the housing member 24, reduce the passageway between the ball valve 26 and the walls of the passageway. Thus, the air flow through the drainage device 1 will be decreased. When the suction from the suction source reaches a high level, the ball valve 26 will seat on valve seat 27 so that the air flow through the regulator 23 will be limited to the air which passes through the restricted passageway 28.

The combination of the air flow regulator 23 and the suction regulator 18 provides for the maintenance of an appropriate suction level within the drainage device and the patient's pleural cavity irrespective of wide fluctuations in the suction from the suction source.

Another embodiment of a suction regulator is shown in FIG. 2. A tubular housing member 29 is provided with a tapered internal passageway with the wider diameter at the lower end and reduced diameter at the upper end similar to the tubular housing member 24 in the FIG. 1 embodiment. There is provided a valve seat 30 at the lower end of the housing member and a valve seat 31 at the upper end. There are provided retainer disks 32 and 33 which are apertured as shown and are press fit within the tubular housing member 29. A guide rod 34 is held by the retainer disks 32 and 33 and has a ball valve 35 slidable on the rod. The ball valve 35 has a central bore 36 therethrough to receive the rod 34. The bore 36 has a considerably larger diameter than the diameter of the rod 34 so that even when the ball valve 35 is seated at the upper end of the tubular housing member 29 on valve seat 30, there is a restricted passageway through the bore 36 in the ball valve 35. The operation of the air flow regulator shown in FIG. 2 is substantially the same as that described with respect to the air flow regulator shown in FIG. 1. The ball valve provides for decreased air flow through the device when the suction level from the suction source increases. The unit thus permits the suction regulator unit 18 to perform the function of maintaining an appropriate suction level within the drainage device and the patient's pleural cavity more accurately at the appropriate level.

Obviously many modifications and variations of the present invention are possible in light of the above teachings.

What is claimed as new and is desired to be secured by Letters Patent is:

1. A suction regulator system for a pleural drainage device having a collection chamber comprising a passageway extending from the collection chamber to an external port in the drainage device, a suction regulator unit in communication with said passageway, said suction regulator unit including means for connecting said passageway with atmosphere, suction tube connected to said external port in the drainage device adapted to be connected to a suction source, and an air flow regulator vertically disposed in said suction tube, said air flow regulator including valve means vertically movable in said air flow regulator to decrease the air flow through the external port as the suction from the suction source increases.

2. A suction regulating system according to claim 1 wherein said suction regulator unit includes a spring pressed valve which opens to atmosphere in response to excessive negative pressure in said passageway.

3. A suction regulating system according to claim 1 wherein said suction regulator unit includes a tapered chamber having an opening in one end thereof and a tapered valve member disposed in said chamber and a spring urging said valve to close said opening.

4. A suction regulating system according to claim 1 wherein said last named means includes a ball valve disposed in a tapered chamber having valve seats at each end of the chamber.

5. An air flow regulator system for a pleural drainage device having a collection chamber comprising a passageway extending from the collection chamber to an external port in the drainage device, a suction regulator unit in communication with said passageway, said suction regulator unit including means for connecting said passageway with atmosphere, a suction tube connected to said external port in the drainage device adapted to be connected to a suction source, and an air flow regulator having a passageway therein extending generally vertical in said suction tube, said air flow regulator including valve means vertically movable in said passageway to decrease the air flow through the external port as the suction from the suction source increases.

6. An air flow regulating system according to claim 5 wherein said suction regulator unit includes a spring pressed valve which opens to atmosphere in response to excessive negative pressure in said passageway.

7. An air flow regulating system according to claim 5 wherein said suction regulator unit includes a tapered chamber having an opening in one end thereof and a tapered valve member disposed in said chamber and a spring urging said valve to close said opening.

8. An air flow regulating system according to claim 5 wherein said last named valve means includes a ball valve movable in said passageway, said passageway having valve seats at each end thereof.

* * * * *